(12) United States Patent
Henkel et al.

(10) Patent No.: US 10,758,155 B2
(45) Date of Patent: Sep. 1, 2020

(54) IMAGING PROBE AND METHOD OF OBTAINING POSITION AND/OR ORIENTATION INFORMATION

(71) Applicant: eZono AG, Jena (DE)

(72) Inventors: Rolf Henkel, Jena (DE); Eliseo Ventura Sobrino Patino, Jena (DE); Robert Von Offenberg Sweeney, Jena (DE); Allan Dunbar, Jena (DE)

(73) Assignee: eZono AG, Jena (DE)

( * ) Notice: Subject to any disclaimer, the term of this patent is extended or adjusted under 35 U.S.C. 154(b) by 0 days.

(21) Appl. No.: 15/365,775

(22) Filed: Nov. 30, 2016

(65) Prior Publication Data

US 2017/0079550 A1    Mar. 23, 2017

Related U.S. Application Data

(62) Division of application No. 14/342,748, filed as application No. PCT/EP2011/065420 on Sep. 6, 2011, now Pat. No. 9,597,008.

(51) Int. Cl.
*A61B 5/05* (2006.01)
*A61B 5/06* (2006.01)
(Continued)

(52) U.S. Cl.
CPC ............ *A61B 5/062* (2013.01); *A61B 8/0833* (2013.01); *A61B 8/14* (2013.01); *A61B 8/4254* (2013.01);
(Continued)

(58) Field of Classification Search
CPC .. G01R 33/02; G01R 33/0206; G01R 35/005; H01F 13/003; H01F 7/0273;
(Continued)

(56) References Cited

U.S. PATENT DOCUMENTS

| 4,317,078 A | 2/1982 | Weed |
| 4,508,119 A | 4/1985 | Tukamoto |

(Continued)

FOREIGN PATENT DOCUMENTS

| AT | 455499 | 2/2010 |
| AT | 492214 | 1/2011 |

(Continued)

OTHER PUBLICATIONS

European Patent Office International Search Report for PCT/EP2011/065420; dated Aug. 20, 2012; 5 pages.

(Continued)

*Primary Examiner* — Mark D Remaly
(74) *Attorney, Agent, or Firm* — Schwabe Williamson & Wyatt, PC

(57) ABSTRACT

A method of obtaining information about the position and/or orientation of a magnetic component relatively to a magnetometric detector, the magnetic component and the magnetometric detector being moveable independently from each other relatively to a static secondary magnetic field, the method comprising the steps of: measuring in the presence of the combination of both the magnetic field of the magnetic component and the static secondary magnetic field essentially simultaneously the strength and/or orientation of a magnetic field at at least a first position and a second position spatially associated with the magnetometric detector, the second position being distanced from the first position; and combining the results of the measurements to computationally eliminate the effect of the secondary magnetic field and derive the information about the position and/or orientation of the magnetic component.

6 Claims, 7 Drawing Sheets

(51) Int. Cl.
*A61B 8/08* (2006.01)
*G01R 33/02* (2006.01)
*G01B 7/00* (2006.01)
*A61B 34/20* (2016.01)
*A61B 8/14* (2006.01)
*A61B 8/00* (2006.01)
*G01R 35/00* (2006.01)
*H01F 13/00* (2006.01)
*H01F 7/02* (2006.01)
*A61B 5/053* (2006.01)

(52) U.S. Cl.
CPC ............ *A61B 8/4494* (2013.01); *A61B 34/20* (2016.02); *G01B 7/003* (2013.01); *G01R 33/02* (2013.01); *G01R 33/0206* (2013.01); *G01R 35/005* (2013.01); *H01F 7/0273* (2013.01); *H01F 13/003* (2013.01); *A61B 5/0536* (2013.01); *A61B 2034/2051* (2016.02)

(58) Field of Classification Search
CPC ............ A61B 2034/2051; A61B 34/20; A61B 5/0536; A61B 5/062; A61B 8/0833; A61B 8/14; A61B 8/4254; A61B 8/4494; G01B 7/003
See application file for complete search history.

(56) References Cited

U.S. PATENT DOCUMENTS

| | | |
|---|---|---|
| 4,855,584 A | 8/1989 | Tomiyama |
| 5,042,486 A | 4/1991 | Pfeiler |
| 5,055,813 A | 10/1991 | Johnson |
| 5,425,382 A | 6/1995 | Golden |
| 5,622,169 A | 4/1997 | Golden |
| 5,694,037 A | 12/1997 | Palstra |
| 5,744,953 A | 4/1998 | Hansen |
| 5,767,669 A | 6/1998 | Hansen |
| 5,831,260 A | 11/1998 | Hansen |
| 5,833,608 A | 11/1998 | Acker |
| 5,879,297 A | 3/1999 | Haynor |
| 5,902,238 A | 5/1999 | Golden |
| 5,941,889 A | 8/1999 | Cermak |
| 5,944,023 A | 8/1999 | Johnson |
| 5,953,683 A | 9/1999 | Hansen |
| 6,052,610 A | 4/2000 | Koch |
| 6,073,043 A | 6/2000 | Schneider |
| 6,101,410 A | 8/2000 | Panescu |
| 6,172,499 B1 | 1/2001 | Ashe |
| 6,198,956 B1 | 3/2001 | Dunne |
| 6,216,028 B1 | 4/2001 | Haynor |
| 6,233,476 B1 | 5/2001 | Strommer |
| 6,246,231 B1 | 6/2001 | Ashe |
| 6,246,898 B1 | 6/2001 | Vesely |
| 6,248,074 B1 | 6/2001 | Ohno |
| 6,263,230 B1 | 7/2001 | Haynor |
| 6,266,551 B1 | 7/2001 | Osadchy |
| 6,310,532 B1 | 10/2001 | Santa Cruz |
| 6,315,724 B1 | 11/2001 | Berman |
| 6,336,899 B1 | 1/2002 | Yamazaki |
| 6,361,499 B1 | 3/2002 | Bates |
| 6,368,280 B1 | 4/2002 | Cermak |
| 6,379,307 B1 | 4/2002 | Filly |
| 6,427,079 B1 | 7/2002 | Schneider |
| 6,438,401 B1 | 8/2002 | Cheng |
| 6,453,190 B1 | 9/2002 | Acker |
| 6,528,991 B2 | 3/2003 | Ashe |
| 6,542,766 B2 | 4/2003 | Hall |
| 6,546,279 B1 | 4/2003 | Bova |
| 6,587,709 B2 | 7/2003 | Solf |
| 6,626,832 B1 | 9/2003 | Paltieli |
| 6,669,635 B2 | 12/2003 | Kessman |
| 6,678,552 B2 | 1/2004 | Pearlman |
| 6,690,159 B2 | 2/2004 | Burreson |
| 6,690,963 B2 | 2/2004 | Ben-Haim |
| 6,716,166 B2 | 4/2004 | Govari |
| 6,733,458 B1 | 5/2004 | Steins |
| 6,754,596 B2 | 6/2004 | Ashe |
| 6,774,624 B2 | 8/2004 | Anderson |
| 6,784,660 B2 | 8/2004 | Ashe |
| 6,785,571 B2 | 8/2004 | Glossop |
| 6,788,967 B2 | 9/2004 | Ben-Haim |
| 6,813,512 B2 | 11/2004 | Aldefeld |
| 6,834,201 B2 | 12/2004 | Gillies |
| 6,856,823 B2 | 2/2005 | Ashe |
| 6,895,267 B2 | 5/2005 | Panescu |
| 6,954,128 B2 | 10/2005 | Humphries |
| 6,980,921 B2 | 12/2005 | Anderson |
| 7,020,512 B2 | 3/2006 | Ritter |
| 7,048,745 B2 | 5/2006 | Tierney |
| 7,090,639 B2 | 8/2006 | Govari |
| 7,197,354 B2 | 3/2007 | Sobe |
| 7,215,990 B2 | 5/2007 | Feussner |
| 7,274,325 B2 | 9/2007 | Fattah |
| 7,275,008 B2 | 9/2007 | Plyvanainen |
| 7,324,915 B2 | 1/2008 | Altmann |
| 7,351,205 B2 | 4/2008 | Szczech |
| 7,373,271 B1 | 5/2008 | Schneider |
| 7,386,339 B2 | 6/2008 | Strommer |
| 7,471,202 B2 | 12/2008 | Anderson |
| 7,505,810 B2 | 3/2009 | Harlev |
| 7,517,318 B2 | 4/2009 | Altmann |
| 7,524,320 B2 | 4/2009 | Tierney |
| 7,551,953 B2 | 6/2009 | Lardo |
| 7,555,330 B2 | 6/2009 | Gilboa |
| 7,558,616 B2 | 7/2009 | Govari |
| 7,561,051 B1 | 7/2009 | Kynor |
| 7,573,258 B2 | 8/2009 | Anderson |
| 7,588,541 B2 | 9/2009 | Floyd |
| 7,603,155 B2 | 10/2009 | Jensen |
| 7,603,160 B2 | 10/2009 | Suzuki |
| 7,610,078 B2 | 10/2009 | Willis |
| 7,618,374 B2 | 11/2009 | Barnes |
| 7,636,595 B2 | 12/2009 | Marquart |
| 7,652,259 B2 | 1/2010 | Kimchy |
| 7,657,298 B2 | 2/2010 | Moctezuma de la Barrera |
| 7,660,623 B2 | 2/2010 | Hunter |
| 7,668,583 B2 | 2/2010 | Fegert |
| 7,671,887 B2 | 3/2010 | Pescatore |
| 7,697,973 B2 | 4/2010 | Strommer |
| 7,706,860 B2 | 4/2010 | McGee |
| 7,722,565 B2 | 5/2010 | Wood |
| 7,749,168 B2 | 7/2010 | Maschke |
| 7,769,427 B2 | 8/2010 | Shachar |
| 7,797,032 B2 | 9/2010 | Martinelli |
| 7,806,824 B2 | 10/2010 | Ohtake |
| 7,809,421 B1 | 10/2010 | Govari |
| 7,819,810 B2 | 10/2010 | Stringer |
| 7,822,464 B2 | 10/2010 | Maschke |
| 7,831,096 B2 | 11/2010 | Williamson, Jr. |
| 7,835,785 B2 | 11/2010 | Scully |
| 7,840,251 B2 | 11/2010 | Glossop |
| 7,840,253 B2 | 11/2010 | Tremblay |
| 7,840,256 B2 | 11/2010 | Lakin |
| 7,873,401 B2 | 1/2011 | Shachar |
| 7,881,769 B2 | 1/2011 | Sobe |
| 7,907,989 B2 | 3/2011 | Borgert |
| 7,909,815 B2 | 3/2011 | Whitmore, III |
| 7,926,776 B2 | 4/2011 | Cermak |
| 7,945,309 B2 | 5/2011 | Govari |
| 7,962,196 B2 | 6/2011 | Tuma |
| 7,966,057 B2 | 6/2011 | Macaulay |
| 7,971,341 B2 | 7/2011 | Dukesherer |
| 7,974,680 B2 | 7/2011 | Govari |
| 7,996,059 B2 | 8/2011 | Porath |
| 8,023,712 B2 | 9/2011 | Ikuma |
| 8,027,714 B2 | 9/2011 | Shachar |
| 8,041,411 B2 | 10/2011 | Camus |
| 8,041,412 B2 | 10/2011 | Glossop |
| 8,041,413 B2 | 10/2011 | Barbagli |
| 8,049,503 B2 | 11/2011 | Kimura |
| 8,060,184 B2 | 11/2011 | Hastings |
| 8,064,985 B2 | 11/2011 | Peterson |

(56) References Cited

U.S. PATENT DOCUMENTS

| | | |
|---|---|---|
| 8,068,897 B1 | 11/2011 | Gazdzinski |
| 8,073,529 B2 | 12/2011 | Cermak |
| 8,079,982 B1 | 12/2011 | Ponzi |
| 8,082,022 B2 | 12/2011 | Moctezuma de la Barrera |
| 8,086,298 B2 | 12/2011 | Whitmore, III |
| 8,088,070 B2 | 1/2012 | Pelissier |
| 8,090,168 B2 | 1/2012 | Washburn |
| 8,106,905 B2 | 1/2012 | Markowitz |
| 8,147,408 B2 | 4/2012 | Bunce |
| 8,162,821 B2 | 4/2012 | Kawano |
| 8,175,680 B2 | 5/2012 | Panescu |
| 8,216,149 B2 | 7/2012 | Oonuki |
| 8,226,562 B2 | 7/2012 | Pelissier |
| 8,228,028 B2 | 7/2012 | Schneider |
| 8,506,493 B2 | 8/2013 | Ostrovsky |
| 2002/0103431 A1 | 8/2002 | Toker |
| 2003/0036695 A1 | 2/2003 | Govari |
| 2003/0220557 A1 | 11/2003 | Cleary |
| 2004/0047044 A1 | 3/2004 | Dalton |
| 2004/0051610 A1 | 3/2004 | Sajan |
| 2004/0106869 A1 | 6/2004 | Tepper |
| 2004/0147920 A1 | 7/2004 | Keidar |
| 2004/0171934 A1 | 9/2004 | Khan |
| 2005/0020919 A1 | 1/2005 | Stringer |
| 2005/0033315 A1 | 2/2005 | Hankins |
| 2005/0101876 A1 | 5/2005 | Pearlman |
| 2005/0107870 A1 | 5/2005 | Wang |
| 2005/0137659 A1 | 6/2005 | Garabedian |
| 2005/0143648 A1 | 6/2005 | Minai |
| 2005/0197569 A1 | 9/2005 | McCombs |
| 2006/0061354 A1 | 3/2006 | Wallance |
| 2006/0072843 A1 | 4/2006 | Johnston |
| 2006/0241397 A1 | 10/2006 | Govari |
| 2006/0247600 A1* | 11/2006 | Yeung ............... A61B 17/00 604/500 |
| 2006/0253107 A1 | 11/2006 | Hashimshony |
| 2007/0016013 A1 | 1/2007 | Camus |
| 2007/0027390 A1 | 2/2007 | Maschke |
| 2007/0049846 A1 | 3/2007 | Bown |
| 2007/0055468 A1 | 3/2007 | Plyvanainen |
| 2007/0163367 A1 | 7/2007 | Sherman |
| 2007/0167801 A1 | 7/2007 | Webler |
| 2007/0185398 A1 | 8/2007 | Kimura |
| 2007/0276240 A1 | 11/2007 | Rosner |
| 2008/0027475 A1 | 1/2008 | Grundmann |
| 2008/0033286 A1 | 2/2008 | Whitmore |
| 2008/0036580 A1 | 2/2008 | Breed |
| 2008/0071172 A1 | 3/2008 | Bruck |
| 2008/0094057 A1 | 4/2008 | Ashe |
| 2008/0134727 A1 | 6/2008 | May |
| 2008/0146939 A1 | 6/2008 | McMorrow |
| 2008/0183071 A1 | 7/2008 | Strommer |
| 2008/0228195 A1* | 9/2008 | von Jako ............ A61B 34/20 606/130 |
| 2008/0249395 A1 | 10/2008 | Shachar |
| 2008/0262338 A1 | 10/2008 | Paitel |
| 2009/0070063 A1 | 3/2009 | Edelstein |
| 2009/0105581 A1 | 4/2009 | Widenhorn |
| 2009/0105584 A1 | 4/2009 | Jones |
| 2009/0105779 A1 | 4/2009 | Moore |
| 2009/0156926 A1 | 6/2009 | Messerly |
| 2009/0184825 A1 | 7/2009 | Anderson |
| 2009/0203989 A1 | 8/2009 | Burnside |
| 2009/0228019 A1 | 9/2009 | Gross |
| 2009/0275833 A1 | 11/2009 | Ikeda |
| 2009/0287443 A1 | 11/2009 | Jascob |
| 2009/0299142 A1 | 12/2009 | Uchiyama |
| 2009/0299176 A1 | 12/2009 | Gleich |
| 2009/0312629 A1 | 12/2009 | Razzaque |
| 2009/0322323 A1 | 12/2009 | Brazdeikis |
| 2009/0326323 A1 | 12/2009 | Uchiyama |
| 2010/0036241 A1* | 2/2010 | Mayse ............... A61B 1/2676 600/435 |
| 2010/0049033 A1 | 2/2010 | Kawano |
| 2010/0049050 A1 | 2/2010 | Pelissier |
| 2010/0079158 A1 | 4/2010 | Bar-Tal |
| 2010/0121189 A1 | 5/2010 | Ma |
| 2010/0121190 A1 | 5/2010 | Pagoulatos |
| 2010/0137705 A1 | 6/2010 | Jensen |
| 2010/0156399 A1 | 6/2010 | Chiba |
| 2010/0174176 A1 | 7/2010 | Nagel |
| 2010/0191101 A1 | 7/2010 | Lichtenstein |
| 2010/0228119 A1* | 9/2010 | Brennan ............ A61B 5/0066 600/424 |
| 2010/0249576 A1 | 9/2010 | Askarinya |
| 2010/0268072 A1 | 10/2010 | Hall |
| 2010/0286517 A1 | 11/2010 | Kamen |
| 2010/0312113 A1 | 12/2010 | Ogasawara |
| 2011/0021903 A1 | 1/2011 | Strommer |
| 2011/0028848 A1 | 2/2011 | Shaquer |
| 2011/0034806 A1 | 2/2011 | Hartov |
| 2011/0054293 A1 | 3/2011 | Markowitz |
| 2011/0060185 A1 | 3/2011 | Ikuma |
| 2011/0081063 A1 | 4/2011 | Leroy |
| 2011/0082366 A1 | 4/2011 | Scully |
| 2011/0118590 A1 | 5/2011 | Zhang |
| 2011/0137152 A1 | 6/2011 | Li |
| 2011/0137156 A1 | 6/2011 | Razzaque |
| 2011/0144476 A1 | 6/2011 | Jolesz |
| 2011/0144524 A1 | 6/2011 | Fish |
| 2011/0184690 A1 | 7/2011 | Iida |
| 2011/0224537 A1 | 9/2011 | Brunner |
| 2011/0230757 A1 | 9/2011 | Elgort |
| 2011/0237945 A1 | 9/2011 | Foroughi |
| 2011/0251607 A1 | 10/2011 | Kruecker |
| 2011/0282188 A1 | 11/2011 | Burnside |
| 2011/0295108 A1 | 12/2011 | Cox |
| 2011/0295110 A1 | 12/2011 | Manzke |
| 2012/0016316 A1 | 1/2012 | Zhuang |
| 2012/0071752 A1 | 3/2012 | Sewell |
| 2012/0108950 A1 | 5/2012 | He |
| 2012/0123243 A1 | 5/2012 | Hastings |
| 2012/0130229 A1 | 5/2012 | Zellers |
| 2012/0130230 A1 | 5/2012 | Eichler |
| 2012/0136251 A1 | 5/2012 | Kim |
| 2012/0143055 A1 | 6/2012 | Ng |
| 2012/0150022 A1 | 6/2012 | Bar-Tal |
| 2012/0197108 A1 | 8/2012 | Hartmann |
| 2012/0232380 A1 | 9/2012 | Pelissier |
| 2012/0259209 A1 | 10/2012 | Harhen |
| 2013/0225986 A1 | 8/2013 | Eggers |
| 2013/0296691 A1 | 11/2013 | Ashe |
| 2014/0002063 A1 | 1/2014 | Ashe |
| 2014/0046261 A1 | 2/2014 | Newman |
| 2014/0058221 A1 | 2/2014 | Old |
| 2014/0107475 A1 | 4/2014 | Cox |
| 2014/0228670 A1 | 8/2014 | Justis |
| 2014/0253270 A1 | 9/2014 | Nicholls |
| 2014/0257080 A1 | 9/2014 | Dunbar |
| 2014/0257104 A1 | 9/2014 | Dunbar |
| 2014/0257746 A1 | 9/2014 | Dunbar |
| 2015/0080710 A1 | 3/2015 | Henkel |
| 2015/0359991 A1 | 12/2015 | Dunbar |
| 2017/0079549 A1 | 3/2017 | Henkel |
| 2017/0079550 A1 | 3/2017 | Henkel |
| 2017/0079551 A1 | 3/2017 | Henkel |

FOREIGN PATENT DOCUMENTS

| | | |
|---|---|---|
| CA | 2 647 432 A1 | 10/2007 |
| CA | 2 659 586 A1 | 12/2007 |
| CN | 102860841 A | 1/2013 |
| DE | 10 2008 013 611 A1 | 9/2009 |
| DE | 10 2010 046 948 A1 | 12/2011 |
| EP | 0 488 987 A1 | 6/1992 |
| EP | 0 747 016 A1 | 12/1996 |
| EP | 0 928 976 A2 | 7/1999 |
| EP | 1 212 001 A2 | 6/2002 |
| EP | 1 377 335 A1 | 1/2004 |
| EP | 1 504 713 A1 | 2/2005 |
| EP | 1 715 788 A2 | 11/2006 |
| EP | 1 727 478 A | 12/2006 |
| EP | 1 804 079 A2 | 7/2007 |
| EP | 1 898 775 A2 | 3/2008 |

(56) References Cited

FOREIGN PATENT DOCUMENTS

| | | |
|---|---|---|
| EP | 1 913 875 A1 | 4/2008 |
| GB | 2 445 699 A | 7/2008 |
| JP | H10512462 | 2/1998 |
| JP | 2000185041 | 7/2000 |
| JP | 2003334191 | 11/2003 |
| JP | 2005-312577 A | 11/2005 |
| JP | 2007203039 | 8/2007 |
| WO | 1996/005768 A1 | 2/1996 |
| WO | 9612439 | 5/1996 |
| WO | 2000/063658 A2 | 10/2000 |
| WO | 2002/000093 A2 | 1/2002 |
| WO | 2006/078677 A2 | 7/2006 |
| WO | 2006/078678 A2 | 7/2006 |
| WO | 2006/124192 A2 | 11/2006 |
| WO | 2007/025046 A1 | 3/2007 |
| WO | 2007/025081 A2 | 3/2007 |
| WO | 2008/035271 A2 | 3/2008 |
| WO | 2008/086832 A1 | 7/2008 |
| WO | 2009/070616 A2 | 6/2009 |
| WO | 2009/089280 A1 | 7/2009 |
| WO | 2010/111435 A1 | 9/2010 |
| WO | 2010/132985 A1 | 11/2010 |
| WO | 2011/043874 A1 | 4/2011 |
| WO | 2011/043875 A1 | 4/2011 |
| WO | 2011/044273 A2 | 4/2011 |
| WO | 2011/085034 A1 | 7/2011 |
| WO | 2011082451 | 7/2011 |
| WO | 2011/095924 A1 | 8/2011 |
| WO | 2011/098926 A1 | 8/2011 |
| WO | 2011/109249 A1 | 9/2011 |
| WO | 2011/114259 A1 | 9/2011 |
| WO | 2011/123661 A1 | 10/2011 |
| WO | 2011/127191 A1 | 10/2011 |
| WO | 2011/150376 A1 | 12/2011 |
| WO | 2012/025854 A1 | 3/2012 |
| WO | 2012/040077 A1 | 3/2012 |
| WO | 2012058461 | 5/2012 |
| WO | 2012/098483 A1 | 7/2012 |
| WO | 2013/034175 A1 | 3/2013 |
| WO | 2011150376 | 4/2013 |
| WO | 2014/135592 A1 | 9/2014 |

OTHER PUBLICATIONS

Placidi, Giuseppe, et al.; "Review on Patents about Magnetic Localisation Systems for in vito Catheterizations"; INFM c/o Department of Health Sciences, University of L'Aquila, Via Vetoio Coppito 2, 67100 L'Aquila, Italy; Recent Patents on Biomedical Engineering 2009, 2, 58-64; Received: Dec. 24, 2008; Accepted: Jan. 9, 2009; Revised: Jan. 12, 2009; 8 pages.

Dorveaux et al.; "On-the-field Calibration of an Array of Sensors"; 2010 American Control Conference; Jun. 30-Jul. 2, 2010; Baltimore, MD; USA; 8 pages.

* cited by examiner

IMAGING PROBE AND METHOD OF OBTAINING POSITION AND/OR ORIENTATION INFORMATION

CROSS-REFERENCE TO RELATED APPLICATIONS

This application is a divisional of U.S. patent application Ser. No. 14/342,748, filed on May 28, 2014, now pending, which is a U.S. National Stage Application of PCT/EP2011/065420, filed Sep. 6, 2011, the disclosures of which are both incorporated herein by reference in their entireties.

FIELD OF THE INVENTION

The invention relates to methods of obtaining information about the position and/or orientation of a magnetic component relatively to a magnetic detector. It further relates to systems of an imaging probe for imaging at least part of the tissue of a patient and a magnetic detector for detecting the position and/or orientation of the magnetic component relatively to the magnetometric detector. It moreover relates to a medical device at least a portion of which is insertable into the tissue of the patient, the medical device comprising a magnetic component, and to a method of obtaining position and/or orientation information about at least a part of a medical device. Finally, the invention relates to an apparatus for magnetizing an elongate medical device.

BACKGROUND OF THE INVENTION

In numerous medical procedures that involve the insertion of a medical device into a patient's tissue, e.g. minimally invasive procedures and local anesthesia, it can be of great advantage for the physician to be informed of the exact position of the medical device in the patient's tissue. For example, to introduce regional anesthesia, including peripheral nerve blocks for surgical anesthesia or postoperative analgesia, a needle can be guided to the region of interest with the help of ultrasound imaging. It has proven challenging, however, to precisely detect the needle's end point in the ultrasound image.

Northern Digital Inc., Ontario, Canada (www.ndigital.com) offers an electromagnetic detection system under the trade name "Aurora". The system comprises a field generator for creating an electromagnetic field and various types of sensor coils that react to the field produced by the generator. One or more of the sensor coils can be embedded into a medical instrument such as a biopsy needle, a catheter or a flexible endoscope for measuring in real time the position of the instrument's tip or, if several coils are embedded, the shape of the instrument. The various types of sensor coils available differ in shape and size and can detect their position relatively to the generator's electromagnetic field in three-dimensional space and their orientation in two or three dimensions. Wires connect the sensor coils with a sensor interface unit that transmits the coils' data to a system control unit. The system control unit collects the information obtained from the sensor coils and calculates their position and orientation.

In "Evaluation of a miniature electromagnetic position tracker", Mat. Phys. (2002), 29 (1), 2205 ff., Hummel et al. have studied the effects of the presence of an ultrasound scan head on the accuracy of the "Aurora" electromagnetic tracking system measurement results.

Placidi, G. et al. in "Review of Patents about Magnetic Localization Systems for in vivo Catheterizations", Rec. Pat. Biomed. Eng. (2009), 2, 58 ff., distinguish between systems where the magnetic field is located outside the patient's body ("extra-body generated magnetic field" as in the "Aurora" system) and systems where the magnetic field is generated by a permanent magnet located inside the patient's body ("intra-body permanent magnet"). A system is discussed that can detect the location in three dimensions and the orientation in two dimensions of a permanent magnet that is permanently fixed to an intra-body medical device. Each measurement involves at least two spatially separated three-axis magnetic sensors in order to measure x-, y- and z-components of the magnetic field produced by the permanent magnet in at least two spatial positions. Six magnetic sensors are arranged in a circle surrounding the patient in order to ensure that each part of the patient's body is covered by at least two of the sensors. Before use, the system is calibrated to take into account the terrestrial magnetic field. In the calibration step, in the absence of the permanent magnet, the terrestrial magnetic field is measured and then subtracted from each subsequent measurement. From the remainder, the position of the magnet is calculated. It is considered a disadvantage of the system that it cannot be moved once calibrated.

Yet, the patent U.S. Pat. No. 6,263,230 B1, which is cited in Placidi et al., supra, B1 describes a "continuous automatic recalibration" scheme with which a detector can be moved after the initial calibration, even though not simultaneously with the magnet. The magnetic detector system is attached to a fluoroscopic head in a known spatial relationship to detect the position of a permanent magnet of an indwelling medical device and the magnet's field is approximated as a dipole field. In order to compensate for the terrestrial magnetic field as well as localized perturbations associated with this field, an initial calibration is performed before the magnet is introduced into the patient. For each magnetic sensor of the detector system an offset value is determined. Later, when the magnet has been introduced into the patient, the offset values are subtracted from the readings of the magnetic sensors, thus compensating for the terrestrial magnetic field and its localized perturbations. Moreover, the "continuous automatic recalibration" scheme allows compensating for the localized perturbations of the terrestrial magnetic field even if the detector system is moved: According to this scheme, the detector is moved while the magnet remains stationary at its position that is known from the previous measurement. The exact positional change of the detector is tracked by a digitizing arm and from this the magnetic field at the detector's new location due to the magnet is calculated. The result is subtracted from the field actually measured by the detector and the remainder is considered the contribution of the terrestrial magnetic field at the new location. The process can be repeated as the detector is moved to yet another location.

U.S. Pat. No. 6,216,029 B1 discloses an apparatus for ultrasound free-hand directing of a needle. Both an ultrasound probe and the needle or a needle guide are provided with orientation sensors for sensing the position of the probe and the needle with respect to a reference. The orientation sensors each may comprise three transponders in triangular alignment. The transponders preferably are electro-optical sensors which operate with infrared or visible light. Alternatively, the system comprises a magnetic transmitter and magnetic receivers attached to an ultrasound probe and the needle or needle guide. On a displays screen, the ultrasound image of a target area is shown. Moreover, the needle is shown as a distinctly coloured line, even if the needle is outside the ultrasound image. In addition or alternatively, a trajectory of the needle is displayed.

Similarly, U.S. Pat. No. 6,733,468 B1 discloses a diagnostic medical ultrasound system in which both an ultrasound probe and an invasive medical device, e.g. a cannula, have location sensors attached to them for sensing their position and/or orientation. From the positions of the needle and the probe the relative position of the needle with respect to the probe's imaging plan is determined. From this, a projected and an actual trajectory of the invasive medical device are calculated and superimposed on the ultrasound image.

Problem to be Solved by the Invention

It is an objective of the present invention to provide improved methods of obtaining information about the position and/or orientation of a magnetic component relatively to a magnetometric detector. The invention further aims to provide improved systems of a imaging probe for imaging at least part of the tissue of the patient and a magnetometric detector for detecting the position and/or orientation of a magnetic component relatively to the magnetometric detector. The invention also seeks to provide an improved medical device at least a portion of which is insertable into the tissue of a patient, the medical device comprising a magnetic component, and to provide an improved method of obtaining position and/or orientation information about at least a part of a medical device. Finally, it is an objective of the invention to provide a new apparatus for magnetizing an elongate medical device.

Solution According to the Invention

In the following, the present invention is described with reference to the claims. Note that the reference numbers in all claims have no limiting effect but only serve the purpose of improving readability.

Methods of Obtaining Position and/or Orientation Information

According to one aspect of the invention, the problem is solved by providing a method where the position and/or orientation of the magnetic component relatively to the magnetometric detector is obtained directly. Advantageously, because the effect of the secondary magnetic field is computationally eliminated by combining the results of the at least two simultaneous measurements, the initial calibration step that is for example used in the method described in U.S. Pat. No. 6,263,230 B1 for obtaining offset values to compensate for the terrestrial magnetic field is no longer required. Also, the "continues automatic recalibration" procedure disclosed therein, which relies on a digitizing arm to measure the detector's positional change and moreover requires that the magnetic components remains stationary while the detector is moved, can be avoided. Rather, the position and/or orientation of the magnetic component can be derived even if the magnetometric detector and the magnetic component are moved simultaneously. This is of considerable benefit, in particular when the magnetometric detector is attached to a hand held probe such as an ultrasound probe for ultrasound-assisted medical procedures to track the position of a medical device relatively to the image created by the probe of the tissue of the patient. In such cases, it is almost impossible for the physician to keep the probe stationary while the medical device is moved. Moreover, as the digitizing arm of U.S. Pat. No. 6,263,230 B1 can be dispensed with, advantageously, the means for detecting the position and/or orientation of a magnetic component according the invention do not require physical contact with a reference. In fact, it is achievable that for providing the desired information about the position and/or orientation of a magnetic component no means as a reference other than the magnetic component is required. This is in contrast not only to the teaching of U.S. Pat. No. 6,263,230 B1 but also to that of e.g. U.S. Pat. No. 6,216,029 B1 and U.S. Pat. No. 6,733,468 B1. As the quantity of interest, namely the position and/or orientation of the magnetic component relatively to the probe, is obtained directly, the estimation is less error-prone than estimation methods that rely on separate estimates for the probe position and the position of the magnetic component, e.g. the methods disclosed in U.S. Pat. No. 6,216,029 B1 and U.S. Pat. No. 6,733,468 B1.

Also advantageously, by combing the results of the two measurements taken essentially simultaneously to obtain the position and/or orientation of the magnetic component, procedures can be eliminated that rely on an oscillating magnetic field of the magnetic component, e.g. the methods disclosed in Placidi, G. et al., supra, in relation to extra-body generated magnetic fields, in order to compensate for the terrestrial magnetic field.

In the context of the present invention, a "magnetometric detector" is a device that can obtain quantitative information about the magnetic field to which it is exposed, such as the absolute value, the direction and/or the gradient of the magnetic field. The magnetometric detector may contain one or more magnetometers. The expression "spatially associated" in relation to the positions at which the measurements take place and the magnetometric detector means that the positions move in synchrony with the detector (and consequently with each other) so that from the location and orientation of the positions that of the detector can be derived.

The "secondary magnetic field" will in general comprise the terrestrial magnetic field. In addition, it might comprise distortions in the terrestrial magnetic field or other magnetic field, e.g. created by apparatus in the vicinity of the magnetometric detector. The preferred secondary magnetic field is essentially homogeneous within the space in which the magnetometric detector moves when used.

A "magnetic component" is an entity that creates its own magnetic field. Due to its magnetic property the magnetic component can provide the magnetometric detector with information about its position and/or orientation.

"Information about the position" of the magnetic component refers to the position in at least one spatial dimension, more preferably in two, more preferably in three dimensions. Similarly, the "information about the orientation" of the magnetic component refers to the orientation in at least one spatial dimension, more preferably in two, more preferably in three dimensions. The obtained information preferably is the position and/or orientation of the magnetic component within a certain resolution. Yet, merely the information as to whether the magnetic component is in an imaging plane of the imaging probe or not would already constitute position information within the scope of the present invention. Moreover, information of whether the magnetic component is in front of or behind the imaging plane constitutes position information.

The problem according to the invention is also solved by providing a method where the measurement of the inertial measurement unit is exploited to derive the orientation or even both the orientation and position of the magnetometric detector. From the result, the orientation or orientation and strength, respectively, of the secondary magnetic field, preferably the terrestrial magnetic field, relatively to the detector can be derived. For this purpose, preferably, in an initial calibration step the orientation or strength and orientation of the secondary magnetic field relatively to the magnetometric detector are measured in the absence of the magnetic component. By tracking the orientation changes of the magnetometric device from the initial calibration position one can calculate the components of a secondary magnetic field which is approximately stationary in space and time.

Within the context of the present invention, an "inertial measurement unit" is a unit that comprises a gyroscope and/or an accelerometer, preferably both. Advantageously, for providing the desired information about the position and/or orientation of a magnetic component no means as a reference other than the magnetic component is required.

Systems of an Imaging Probe and a Magnetometric Detector

According to another aspect of the invention, the problem according to the invention is moreover solved by providing a system including an imaging probe for imaging at least part of the tissue of a patient and a magnetometric detector for detecting the position and/or orientation of a magnetic component relative to the magnetometric detector, characterized in that the imaging probe is a hand held probe.

A "hand held probe" is a probe that the use is intended for the user to be held in the desired position by hand. In particular, in a hand held probe, technical means such as a support arm, a runner or a wire are lacking that would hold the probe in position should the user remove his or her hand. The preferred hand held probe comprises a handle.

Further, the problem according to the invention is solved by providing a system with an imaging probe for imaging at least part of the tissue of a patient and a magnetometric detector for detecting the position and/or orientation of a magnetic component relatively to the magnetometric detector, characterized in that the system further comprises at least one fastener for removably attaching the imaging probe to the magnetometric detector. Due to the fastener, the magnetometric detector according to the invention can be attached to an imaging probe that was originally not designed for the use (or at least not the exclusive use) with the magnetometric detector according to the invention. Preferably, the fastener is fixedly attached to the imaging probe and/or the magnetometric detector. Fasteners may also be provided as separate parts and may comprise a portion (e.g. self-adhesive of portion) for fixedly attaching the fastener to the imaging probe and/or the medical device.

Medical Device and Method of Obtaining Position and/or Orientation Information about the Medical Device According to yet another aspect of the invention, the problem is also solved by means of providing a medical device with at least a portion which is insertable into the tissue of a patient, the medical device comprising a magnetic component that is integral with or removably attached to the tissue-insertable portion of the medical device, characterized I that the magnetic component is a functional component of the medical device, and a method of obtaining position and/or orientation information about at least a part of a medical device by permanently magnetizing a functional component of the medical device by exposing the functional component to a magnetic field; and detecting position and/or orientation information either of magnetic component by means of a magnetometric detector. The medical device and the method of obtaining position and/or orientation information about at least a part of a medical device exploit the inventors' finding that many medical devices comprise functional components, e.g. a cannula or a metal rod, which can be magnetized in order to render the medical device detectable by a magnetometric detector. The functional component of the medical device can therefore simply by means of magnetization be assigned to an additional purpose beyond its original function in the medical device.

In the context of the present invention, a "functional component" of the medical device is a component that in addition to providing the magnetometric detector with position and/or orientation information also contributes to the functioning of the medical device, i.e. it contributes to the medical device serving its purpose as a medical device. In this regard, forwarding position and/or orientation information to the magnetometric detector is not considered a function of the medical device. The function may e.g. be the transport of a fluid into or out of the patient's tissue if the medical device is a catheter or a cannula, or the function may be an electrosurgical treatment if the medical device is an electrosurgical instrument.

The preferred magnetic component is an "essential" component of the medical device. In this context, "essential" means that the medical device cannot fulfil its purpose when the magnetic component is removed. Alternatively, the magnetic component is not essential but nevertheless beneficial. It may for example improve the functionality, the handling or other properties of the medical device beyond providing orientation and/or position information to the magnetometric detector.

Magnetization Apparatus

Finally, according to a further aspect of the invention, the problem is solved by providing an apparatus for magnetizing an elongate medical device with a reservoir for keeping the elongate medical device and a magnet for magnetizing the elongate medical device. The apparatus can be used to magnetize the elongate medical device, e.g. a cannula, just before a medical procedure is performed. Due to the apparatus comprising both a reservoir for keeping the elongate medical device and a magnetizer, cannula can easily be magnetized by e.g. a physician in order to turn them into magnetic components for use in the methods, with the system and in the medical device according to the invention.

While for better understanding of the fundamental concepts of the invention throughout the present description and the claims reference is made only to one magnetic component, the invention in all its aspects of course also encompasses embodiments in which in addition further magnetic components are present. As is readily apparent to those skilled in the art, the methods, apparatus and systems according to the invention can equally be applied to multiple magnetic components instead of only one magnetic component.

DESCRIPTION OF PREFERRED EMBODIMENTS OF THE INVENTION

Preferred features of the invention which may be applied alone or in combination are discussed in the following as well as in the dependent claims.

Obtaining Position and/or Orientation Information

Preferably, the strength and/or orientation of the magnetic field as measured at one or more of the positions spatially associated with the magnetometric detector is used as a direct estimate of the strength and/or orientation of the secondary magnetic field, i.e. the (possibly distorted) terrestrial magnetic field. For this purpose, preferably, these position or positions are separated far enough away from the magnetic component to ensure that the measurement at this/these position(s) is sufficiently unaffected by the magnetic component's magnetic field to directly provide an estimate of the strength and/or orientation of the secondary magnetic field. Therefore, if the magnetometric detector is integral with or attachable to a imaging probe, e.g. an ultrasound imaging probe, as discussed further below, the means (e.g. magnetometers) of the magnetometric detector for measuring the strength and/or orientation of the secondary magnetic field according to the present embodiment of the invention is/are sufficiently remote from the part of the imaging probe that is closest to the patient to ensure that the magnetometer(s) is/are essentially unaffected by the magnetic field of the magnetic component introduced into the patient's tissue.

In the context of this embodiment "direct estimate" means that the measurements at the position or positions are sufficient to estimate, within the required accuracy, the strength and/or orientation of the secondary magnetic field.

Advantageously, the magnetic field as measured according to the above preferred embodiment of the present invention can simply be subtracted from the result of the measurement at one or more other position(s) in order to obtain for each of these other measurements the magnetic field of the magnetic component only. This can then be used to derive the position and/or orientation of the magnetic component.

Preferably, the position and/or orientation of the magnetic component is computed by fitting a model of the magnetic field due to the magnetic component to the actual magnetic field of the magnetic component as obtained from the measurements at the positions affected by magnetic component's field after the secondary magnetic field has been subtracted. Thus, position and/or orientation of the magnetic component are the unknown parameters in the model fitting procedure.

In an alternative embodiment of the inventions, a model that comprises the secondary magnetic field, preferably a homogenous magnetic field representing the terrestrial magnetic field, is a further unknown parameter in a model, and the model is fit by a suitable algorithm to the results of the measurements at the positions in order to derive the unknown parameters, i.e. the position and/or orientation of the magnetic components and, if of interest, also the strength and/or orientation of the secondary magnetic field. This method is preferably employed if all positions of the magnetometric detector at which the strength and/or orientation of the magnetic field is measured are considered to be potentially affected by secondary magnetic field to a degree that none of them can directly provide an estimate of the strength and/or orientation of the secondary magnetic field.

In a variation of the above method, the effect of the secondary magnetic field on the results of the measurements at the positions is first cancelled out by determining differential values of the measurements at different positions. For example, after normalization (as discussed below), the average of the strength and/or orientation of the magnetic field determined at the various positions can be subtracted from the strength and/or orientation of the magnetic field at each individual position. Hence, in effect the magnetometers function as gradiometers. These differential values can then be fit to a model that utilizes differentials or other functional derivatives of the original magnetic field.

Moreover, preferably, from the measurements, the change in orientation and/or position of the magnetometric detector due to a movement of the magnetometric detector is obtained. For example, the change in orientation and/or position of the magnetometric detector can be obtained from the orientation of the detector relatively to the terrestrial magnetic field as computed from combining the results of the measurements at two or more positions of the magnetometric detector. Also, the orientation and position of the magnetometric detector can be derived from the measurements of an inertial measurement unit. If the magnetometric detector is attached to an imaging probe, this information can be used, for example, to combine the images acquired by the imaging probe at different positions and/or in different orientations into a three-dimensional map or a panoramic map. In particular, this may facilitate three-dimensional mapping of extended volumes. Thus, the inertial measurement unit, in particular the accelerometer, on one hand and the measurement of the strength and/or orientation of the magnetic field for estimating the secondary magnetic field on the other hand can substitute each other. However, the invention also comprises embodiments in which both of these means are provided. In particular, the results of both means can be combined, e.g. averaged, to improve accuracy.

The Magnetometric Detector and the Base Unit

In the magnetometric detector the strength and/or orientation of the magnetic field preferably is measured, in at least two positions, more preferably at least three, more preferably at least four positions spatially associated with the magnetometric detector, the positions being distanced from each other. The measurements may be combined to derive the position and/or orientation of the magnetic component. They may be moreover combined to computationally eliminate the effect of the secondary magnetic field.

Preferably, the magnetic field in at least two positions, more preferably at least three, more preferably at each of the positions is measured by a magnetometer of the magnetometric detector, each magnetometer being located at the respective position. Preferably, at the first position, more preferably also at the second position, more preferably also at the third position, more preferably at all positions of the magnetometric detector the components of the magnetic field in at least two linearly independent spatial directions, more preferably in all three linearly independent spatial directions are measured.

In a preferred embodiment of the invention, the results of the measurements are transmitted to a base unit for processing, the preferred base unit being separate from the magnetometric detector. In this context, "separate" means that the base unit and the magnetometric detector do not move in synchrony with each other; in other words, they are not spatially associated. Rather, the magnetometric detector can move independently of the base unit. In particular, the base unit can remain stationary while the magnetometric detector (preferably attached to the imaging probe as discussed above) is moved. The transmission between the magnetometric detector and the base unit can be realised, for example, by a flexible cable or by a wireless connection. It is an advantage of the wireless connection that the magnetometric detector can be attached to a conventional imaging probe without requiring another cable in addition to the probe cable.

It is an achievable advantage of this embodiment of the invention that a large part or even all of the computation required to derive from the results of the measurements the position and/or orientation of the magnetic component can be performed in the base unit. This is of benefit in view of the fact that the computational means required for eliminating the effect of the secondary magnetic field and deriving the position and/or orientation of the magnetic component can be too demanding for a microprocessor small enough to be easily attached to the imaging probe. Therefore, by shifting part or all of the computation to the base unit where sufficient processing power can more easily be provided, the magnetometric detector can be kept small and light.

In another embodiment, the base unit is merged with the imaging system, with the information from the magnetometers delivered through the probes cable.

A preferred magnetometric detector comprises several magnetometers, possibly along with an inertial measurement unit, and interface circuitry which might be a multiplexer or a microprocessor. The interface circuitry enables to pass the signals of multiple probes through a single cable or wireless link. It samples the magnetometers (and the inertial measurement unit if present) and possibly monitors other information such as a state of charge of a battery of the magnetometric detector. By means of a transmitter of the magnetometric detector, this information is then transmitted to a receiver of the base unit.

In a preferred embodiment of the invention the magnetometric detector moreover receives information from the base unit. Thus, preferably, two-way communication is possible between the magnetometric detector and the base unit. The return channel from the base unit to the magnetometric detector can for example be used to reconfigure the magnetometers or the inertial measurement unit remotely from the base unit. For example, the working range of the magnetometers can be adapted to the strength of the magnetic components' magnetic field, in particular to avoid overflows in the measurement process.

For transmission, the magnetometric detector and the base unit are functionally connected with each other. The term "functionally connected" encompasses both a direct connection and an indirect connection through one or more intermediate components, which intermediate components may be hardware and/or software components. Preferably, the transmission between the magnetometric detector and the base unit is encoded in a way to prevent eavesdropping, e.g. by means of asymmetrical encryption. Moreover, preferably measures are taken to prevent interference in the case several systems comprising a magnetometric detector and a base unit are operated in close vicinity.

Preferably, in a calibration step, the magnetometers are calibrated with regard to gain, offset and orientation so that in a homogeneous magnetic field they all yield essentially identical measurements. Thereby it is ensured that all magnetometers measure equal values when exposed to a homogeneous field. For example, a magnetometer rotated in the homogeneous terrestrial magnetic field should, depending on the orientation of the magnetometer, measure varying strengths of the components of the magnetic field in the three linearly independent directions. The total strength of the field, however, should remain constant regardless of the magnetometer's orientation. Yet, in magnetometers available on the market, gains and offsets differ in each of the three directions. Moreover, the directions oftentimes are not orthogonal to each other. As described for example in U.S. Pat. No. 7,275,008 B2 for a single sensor, if a magnetometer is rotated in a homogeneous and constant magnetic field, the measurements will yield a tilted 3-dimensional ellipsoid. Because the measured field is constant, however, the normalized measurements should lie on a sphere. Preferably, an offset value $\beta$ and a gain matrix M are introduced to transform the ellipsoid into a sphere.

With a set of sensors, additional steps need to be taken to assure that the measurements of different sensors are identical with each other. To correct for this, preferably, set of a gain normalisation matrices $M_k$ and a normalisation offset vectors $\beta_k$ for each position k are determined which transform the magnetometer's raw results $a_k$ into a normalized result $b_k$:

$$b_k = a_k * M_k + \beta_k$$

Such a set of gain matrices $M_k$ can be obtained by known procedures, for example the iterative calibration scheme described in Dorveaux et. al., "On-the-field Calibration of an Array of Sensors", 2010 American Control Conference, Baltimore 2010.

By virtue of the defined transformation, $b_k$ provides the strength of the component of the magnetic field in three orthogonal spatial directions with equal gain. Moreover, it is ensured that these directions are the same for all magnetometers in the magnetometric detector. As a result, in any homogeneous magnetic field, all magnetometers yield essentially identical values.

The normalisation information $M_k$ and $\beta_k$ for each magnetometer as obtained in the calibration step can be stored either in the magnetometric detector itself or in the base unit. Storing the information in the magnetometric detector is preferred as this allows easy exchange of the magnetometric detector without the need to update the information in the base unit. Thus, in a preferred embodiment of the invention, the magnetometers of the magnetometric device are sampled and their results are normalised in the magnetometric detector. This information, possibly together with other relevant information, is transmitted to the base unit for further analysis.

In another embodiment of the invention, the transformation can be another, more general non-linear transformation $b_k = F(a_k)$.

In addition to the above calibration method, another calibration method is applied which employs an inhomogeneous magnetic field to obtain the relative spatial locations of the magnetometric detector's magnetometers. While standard calibration methods utilize a homogenous magnetic field to (a) align the measurement axis of the magnetometers orthogonally, (b) cancel the offset values and (c) adjust to equal gain, it is of further advantage to the described systems that also the precise relative spatial locations of the magnetometers are available. This can be achieved by an additional calibration step in which the magnetometric detector is subjected to a known inhomogeneous magnetic field. Preferably, comparing the obtained measurements at the various positions to the expected field strengths and/or orientations in the assumed locations, and correcting the assumed locations until real measurements and expected measurements are in agreement, allows for the exact calibration of the spatial positions of the sensor.

In a variation of the latter calibration method, an unknown rather than a known homogenous magnetic field is used. The magnetometers are swept through the unknown magnetic field at varying positions, with a fixed orientation. With one of the magnetometers supplying a reference track, the positions of the other magnetometers are adaptively varied in such a way that their measurements align with the measurements of the reference unit. This can be achieved for example by a feedback loop realizing a mechano-magnetic-electronical gradient-descent algorithm. The tracks used in this inhomogeneous field calibration can also be composed of just a single point in space.

The Imaging Probe and the Processing Unit

Preferably, the magnetometric detector is integral with or removably attachable to an imaging probe for imaging at least part of the tissue of a patient. "Integral" means that the magnetometric detector is permanently fixed to the imaging probe in a way that, if the imaging probe is used as intended, the magnetometric detector cannot be removed from the imaging probe. It may, for example, be located inside a housing of the imaging probe. The magnetometric detector may even be joined with the imaging probe to a degree that for the purpose of service or repair it cannot be separated from the imaging probe without destroying the imaging probe. Yet, the term "integral" also encompasses embodiments in which the magnetometric detector can be removed from the imaging probe for the purpose of repair or maintenance. Within the context of the present invention, "removably attached" means that one part can be removed from the other part to which it is attached by a user if the device is used as intended. Thus, for example, while the magnetometric detector remains attached to the imaging probe to be spatially associated to it during a medical procedure, after the medical procedure has been finished, the detector can be removed from the probe to be attached to another imaging probe for another medical procedure. Preferably, for the purpose of removable attachment, at least one of the magnetometric detector and the imaging probe, preferably both are provided with one or more fasteners. Preferably, the magnetometric detector and the imaging probe are attached to each other in a way that ensures that during use in a medical procedure they are in a fixed position relatively to each other.

The preferred imaging probe is an ultrasound imaging probe. Such an ultrasound imaging probe preferably includes an array of ultrasound transducers. With the aid of the transducers, ultrasound energy, preferably in the form of ultrasound pulses, is transmitted into a region of the patient's tissue to be examined. Subsequently, reflected ultrasound energy returning from that region is received and registered by the same or other transducers. Yet, the present invention may also be used with other types of imaging probes, for example impedance imaging probes, including probes of the kind disclosed in U.S. Pat. No. 7,865,236 B2 to Nervonix Inc.

Other suitable imaging probes include IR sensors or cameras able to measure blood flow and/or other scanning devices.

Moreover, preferably, a processing unit is provided. The position-related information produced by the magnetometric detector and the image information produced by the imaging probe preferably is transmitted from the magnetometric detector and the imaging probe, respectively, to the processing unit (the position-related information preferably via the base unit as discussed above). The information may then be combined in the processing unit to generate an image of the tissue of the patient in which image the position of at least a part of a medical device is indicated based on the position and/or orientation information obtained from the magnetometric detector. The preferred processing unit comprises a display device for displaying the image. In this context, "position-related information" may for example be the raw data obtained by the magnetometers, the calibrated data or actual positions and orientations computed as discussed above. Similarly, "image data" may be raw data obtained by the imaging probe or raw data that has been further processed.

In a preferred embodiment of the invention, the processing unit drives the imaging probe and interprets the raw data received from the imaging probe, e.g. the ultrasound probe. Moreover, preferably, a cable or a bundle of cables is provided to connect the imaging probe with the processing unit. If the imaging probe is an ultrasound probe, the processing unit preferably comprises a driver circuitry to send precisely timed electrical signals to the transducers of the imaging probe in order to generate ultrasound pulses. As part of the ultrasound pulses is reflected from the region to be examined and returns to the ultrasound probe, the received ultrasound energy is converted into electrical signals which are then forwarded to the processing unit. The processing unit amplifies and processes the signals to generate an image of the examined region of the patient's tissue.

As the medical device's positional information is obtained by detecting the position of the device's magnetic component, the part of the medical device, the position of which is indicated, preferably will either be the magnetic component or another component of the medical device, the position of which relatively to the magnetic component is known. In one embodiment of the invention, only a section of the magnetic components is shown, for example the most distal section, such as the distal tip of a cannula.

For transmission of the information from the magnetometric detector and the imaging probe (preferably via the base unit) to the processing unit, the former components are functionally connected with the processing unit. Preferably, the processing unit is further functionally connected to the magnetometric detector (preferably via the base unit) to receive information from the base unit. This way, relevant information may be transmitted from the processing unit or the magnetometric detector to facilitate the computation that takes place therein.

It can be most useful if the image generating processing unit is connected in a bi-directional way. Information obtained by processing the recorded image, preferably in the processing unit, can be transferred to the base unit to facilitate the estimation of the needle position, and vice versa. For example, a Hough-Transformation on a raw ultrasound image might detect a faint image of a needle; this localization information from the ultrasound image can be applied as constraint to the optimization step deriving the same needle position from the magnetometer data. Of course, needle detection algorithms operating directly on the image can as well be stabilized through the information about needle positions coming from the base unit.

Preferably, in the image it is indicated whether the medical device or part of the medical device is located inside or outside a pre-determined spatial plane. Preferably, on the display the image of the patient's tissue in a certain plane is displayed which is identical to the pre-determined spatial plane. The displayed plane may for example be determined by the position and/or orientation of the imaging probe. For example, if the imaging probe is an ultrasound imaging probe that operates in a 2D-mode, the displayed plane is the probe's imaging plane. Preferably, if multiple sections of a medical device are displayed, it is indicated which of the sections is located in the spatial plane, which is located on one side of the spatial plane and which is located on the other side of the spatial plane. For example, the imaging plane of the imaging probe can be associated with one colour, one side of the imaging probe with another colour and the other side with a third colour. Alternatively, or in addition, a trajectory of a part of the magnetic component or medical device may be displayed, for example as disclosed in U.S. Pat. No. 6,733,458 B1. In case the imaging device is primarily a 3D device, the above description is naturally extended to 3D-volumes. Thus, in particular in such case it may be indicated in the image whether the medical device or part of the medical device is located inside or outside a pre-determined volume, and on the display the image of the patient's tissue in a certain volume may be displayed which is identical to the pre-determined spatial volume. The displayed volume may for example be determined by the position and/or orientation of the imaging probe.

The Magnetic Component and the Medical Device

The magnetic component preferably is integral with the remaining medical device. Alternatively, it may be a replaceable part, for example the cannula of a syringe.

The function of the medical device preferably does not depend on the magnetic component being magnetic. In other words, even if the component were not magnetic, the medical device would still perform its purpose. For example, a cannula is not required to be magnetic to serve its purpose of introducing a fluid into the tissue of the patient. This embodiment of the invention exploits the fact that certain components of medical devices, that in general are not magnetic, nevertheless have the potential to be magnetized and can then serve as magnetic components for providing positional and/or orientation information to a magnetometric detector.

Alternatively, the magnetic component is a functional component and the function depends on the component being magnetic. In this case, the invention exploits the fact that the magnetic component in addition to serving its magnetism-related function in the medical device can also be used for providing position and/or orientation information.

The inventors have found that magnetic components, in particular such of medical devices, can reliably be detected by conventional magnetometers available on the market. The magnetic component's magnetic field preferably is not alternating, i.e. it does not periodically change its sign or orientation. The preferred magnetic component's magnetic field is not varying in the sense that it keeps its orientation and/or absolute value with respect to the medical instrument tracked essentially constant during an examination, treatment or surgery. It has been found that such magnetized medical instruments keep their magnetization sufficiently constant during a typical medical procedure to be reliably detected by the magnetometric detector.

The preferred magnetic component is at least partly a permanent magnet. Within the context of the present invention, a "permanent magnet" is an object that is magnetized, thereby creating its own persistent magnetic field due to magnetic remanence. Advantageously, since the magnet is permanent, no power source is required.

While a permanent magnet is preferred, the invention also encompasses embodiments in which the magnetic component is a non-permanent magnet, e.g. an electromagnet, e.g. a solenoid to which an electric current can be applied to create the magnetic field. Moreover, in some embodiments of the invention part of the magnetic component may merely be magnetic due to magnetic induction from another part of the magnetic components, e.g. a permanent magnet-part of the component, while in other embodiments of the invention such induction does not play a role. The part of the magnetic component inducing the magnetic field in the other part must not necessarily be integral with the other part. Rather, the two parts may be separates. Nor must the two parts necessarily be adjacent to one another, but they can also be at a distance from each other. In fact, in general, the magnetic component can comprise not only one but several separate parts that can be distanced from each other, e.g. several permanent magnets arranged in a row in a medical device. Yet, a component of the medical device that is magnetic merely due to induction from outside the medical device, e.g. a coil of a radio-frequency antenna, does not create its own magnetic field and is therefore not considered a magnetic component within the context of the present invention.

The magnetic components or part of the magnetic components may be a magnetic coating. Preferably, the coating is a permanently magnetic coating. For this purpose, it may for example comprise permanently magnetic particles, more preferably nanoparticles. A "nanoparticle" is a particle that in at least two spatial dimensions is equal to or smaller than 100 nm in size.

In one embodiment of the invention, the magnetic component has an essentially uniform magnetization. In another embodiment, the magnetization is non-uniform in at least one dimension, i.e. the magnetic moment varies in magnitude and/or direction as a function of the location on the magnetic component, thereby creating a one- or more-dimensional magnetic pattern, e.g. similar to the pattern of a conventional magnetic memory strip (at least one-dimensional) or disk (two-dimensional) as it is used for the storage of information e.g. on credit cards. In a preferred embodiment of the invention, a one-dimensional magnetic pattern may be recorded along the length of an elongate magnetic component, e.g. a cannula. Advantageously, such a pattern can be useful to identify the magnetic component and thus a device to which it is attached or which it is part of, e.g. the medical device, for documentation purposes. Also, by marking certain parts of the medical object with different magnetic codes, these parts can be distinguished. It is an achievable advantage of this embodiment of the invention that the position and/or orientation of the magnetic component can be better determined, as individual parts of the component can be identified and individually tracked with respect to their position and/or orientation. In particular, advantageously, a varying shape of the magnetic component, for example a needle bending under pressure, can be tracked. Moreover, a deformed magnetic component and/or the component's deformation or degree of deformation can be determined more easily.

The preferred medical device is elongate, i.e. it is at least twice as long as it is wide. More preferably, at least the part of the medical device insertable into the patient's tissue is elongate.

Preferably, at least the part of the medical device that is insertable into the tissue of the patient, more preferably the entire medical device, is tubular. Moreover, preferably the magnetic component is partially tubular. Alternatively, the part of the medical device that is insertable into the tissue of the patient or the medical component may have a non-tubular shape, for example that of a rod, e.g. if the medical device is an electrosurgical instrument. In a preferred embodiment of the invention, at least the part of the medical device that is insertable, more preferably the entire medical device is a cannula. Moreover, the cannula also constitutes the magnetic component. The preferred cannula has a bevelled end with which it is introduced into the patient's tissue.

The invention can particularly favourably be used with such cannulae, as they bend easily and therefore the position of the inserted part of the cannula, in particular the cannula tip, cannot easily be determined from the position of a needle guide as disclosed in U.S. Pat. No. 6,216,029. As shown in the detailed description below, in a preferred embodiment of the invention the model field utilized assumes only two spaced-apart magnetic charges, one being the needle tip. It has been found that for moderate needle bending, as it normally occurs, the deviations of the real field from the model field are relatively small; thus the above model can readily be applied for estimating the needle tip's position even if the needle is bent.

The invention can particularly advantageously be employed with cannula for regional anaesthesia. It may, however, also be employed with biopsy cannulae and catheters, e.g. catheters for regional anaesthesia. The preferred solid material of the cannula or catheter is permanently magnetized or the cannula or catheter is provided with a magnetic coating as described above. Alternatively or in addition, the cannula or catheter may be provided with a solenoid coil, preferably at its distal tip.

The Magnetization Apparatus

The preferred apparatus for magnetizing an elongate medical device comprises a magnetization opening. The magnet preferably is located in the vicinity of the magnetization opening to magnetize the elongate medical device as it passes through the opening. Preferably the opening in the apparatus is an opening in the reservoir, through which opening the elongate medical device can be withdrawn from the reservoir so that when the elongate medical device is removed from the reservoir it is magnetized. Preferably, the elongate medical devices are kept in a sterile packaging different from the reservoir while they are stored in the reservoir. Preferably, they remain in this packaging while they are magnetized.

The preferred elongate medical device is a cannula a rod or a needle. The preferred reservoir can hold more than one elongate medical device simultaneously.

The magnet preferably is an electromagnet, e.g. a solenoid, more preferably a ring-shaped solenoid electromagnet. Alternatively, it may be a permanent magnet. The magnetizing device can be designed to uniformly magnetize the inserted medical device, or to record a magnetized pattern along the elongated medical object. This, for example, may be useful to identify the medical object used for documentation purposes as discussed above. Preferably, a variation of the magnetisation along the length of the elongate medical device can be achieved by varying the solenoid's magnetic field as the elongate medical device progresses through the magnetization opening. To control the variation of the magnetic field, the progress of the elongate medical device can for example be recorded by a measurement roll that is in contact with the elongate medical device when it passes through the magnetization opening. In another embodiment, the magnetization device is a hollow tube made up of separate segments of the magnet. By applying different currents to different sections of the tube, a magnetic pattern can be inscribed on the medical instrument.

The apparatus may be further developed into a calibration tool by providing markings on the apparatus for alignment of the magnetometric detector and the elongate medical device. Preferably, for alignment the magnetometric detector is integral with or attached to the imaging probe and the imaging probe is aligned with the elongate medical device using the markings. Thus, the magnetometric detector is aligned with the medical device via the imaging probe.

By virtue of the markings, the elongate medical device and the magnetometric detector can be put in a well-defined relative position. From this, based on the measurements of the magnetometric device specific parameters of the elongate medical device, most preferably its length and magnetic momentum can be measured for facilitating the later computation of the position and orientation of the cannula during the medical procedure. In fact, these parameters can greatly enhance fitting a model to the parameters measured by the magnetometers as described above.

BRIEF DESCRIPTION OF THE DRAWINGS

The invention is illustrated in greater detail with the aid of schematic drawings.

DETAILED DESCRIPTION OF EMBODIMENTS
OF THE INVENTION

Figure 1:
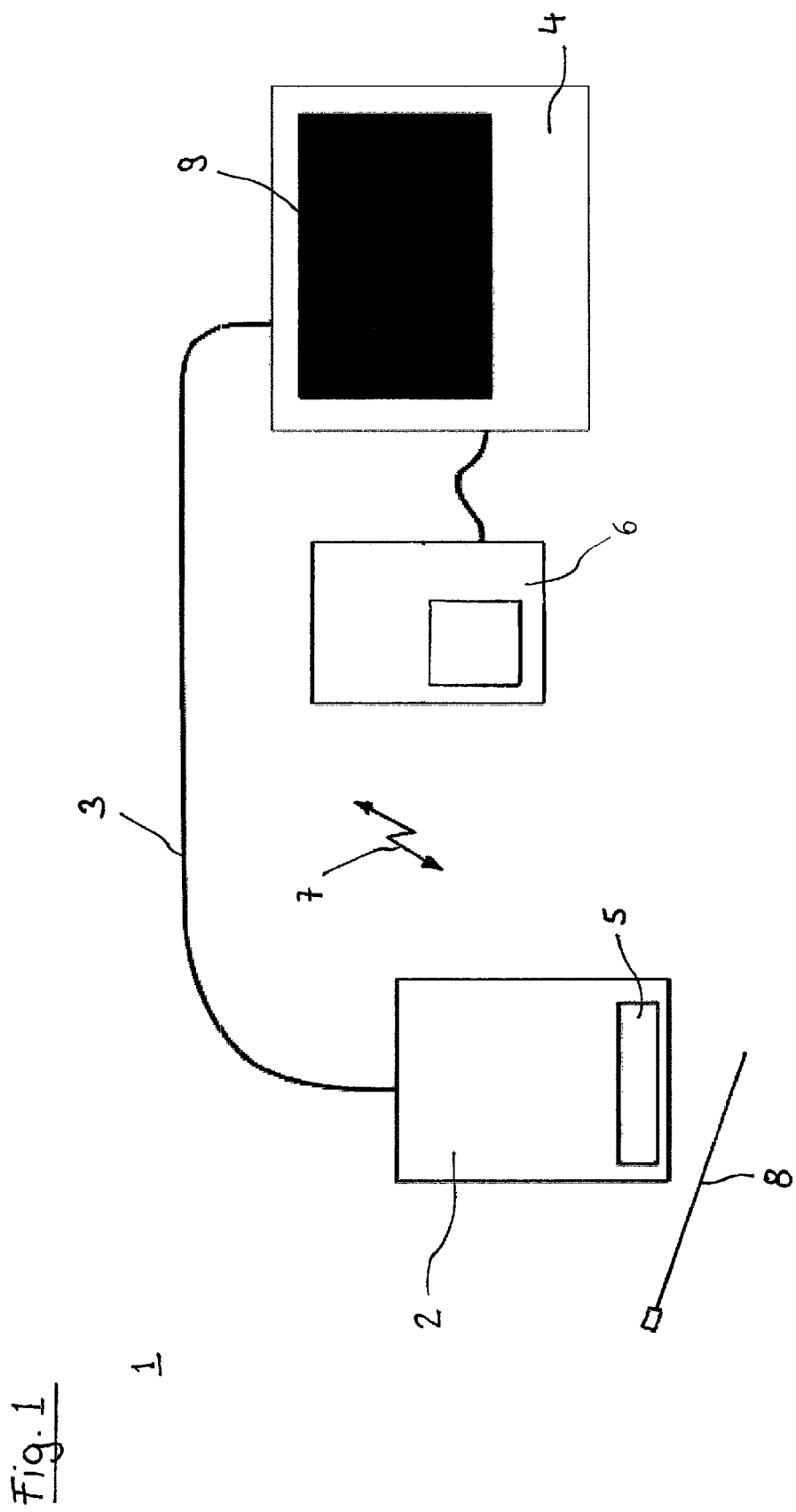
FIG. 1 shows schematically an imaging system comprising an imaging probe, a magnetometric detector and a medical device according to the invention.

The imaging system 1 shown in FIG. 1 comprises a hand held ultrasound probe 2 as an imaging probe connected via a cable 3 with a processing unit 4. The processing unit 4 drives the ultrasound probe 2, i.e. it sends electrical signals to the ultrasound probe 2 to generate ultrasound pulses and interprets the raw data received from the ultrasound probe 2 to assemble it into an image of the patients tissue scanned with the ultrasound probe 2. Moreover a battery operated magnetometric detector 5 is, by means of a Velcro fastener (not shown) attached to the ultrasound probe 2. Positioning elements are provided on the magnetometric detector 5 to ensure that whenever it is attached anew to the ultrasound probe 2 it is always attached in the same well-defined position and orientation.

The magnetometric detector 5 comprises magnetometers 14, 15 (not shown in FIG. 1) and is wirelessly or by other means connected with a base unit 6 in a bi-directional manner (indicated by the flash symbol 7). For this, both the magnetometric detector 2 and the base 6 unit are provided with wireless transceivers. The transceivers may for example employ the Bluetooth™ standard or a standard from the WiFi (IEEE 802.11) family of standards. The base unit 6 receives the normalized results of the measurements of the magnetometric detector 2 and from this calculates the position or, in some embodiments the position and orientation of a magnetic medical cannula 8. Along with the measurement results, additional information such as the state of charge of the magnetometric detector's 5 battery is transmitted from the magnetometric detector 5 to the base unit 6. Moreover, configuration information is transmitted from the base unit 6 to the magnetometric detector 5.

The base unit 6 forwards the result of its calculation, i.e. the position or in some embodiments the position and orientation information, to the processing unit 4. For this purpose, the base unit 6 may for example be connected with the processing unit 4 via a standardized serial connector such as a USB™ (Universal Serial Bus) connector, a FireWire™ (also referred to as iLink™ or IEEE1394) connector or a Thunderbolt™ (also referred to as Light Peak™) connector. In the processing unit 4, the information received from the base unit 6 and the ultrasound image are combined to generate on a display screen 9 of the processing unit 4 an image of the tissue of the patient in which the current position of the cannula 8 in the tissue is indicated. Moreover, the base unit 6 receives configuration information and/or a prior information about the position of the cannula 8 from the processing unit 4 through the same connection.

Figure 2:
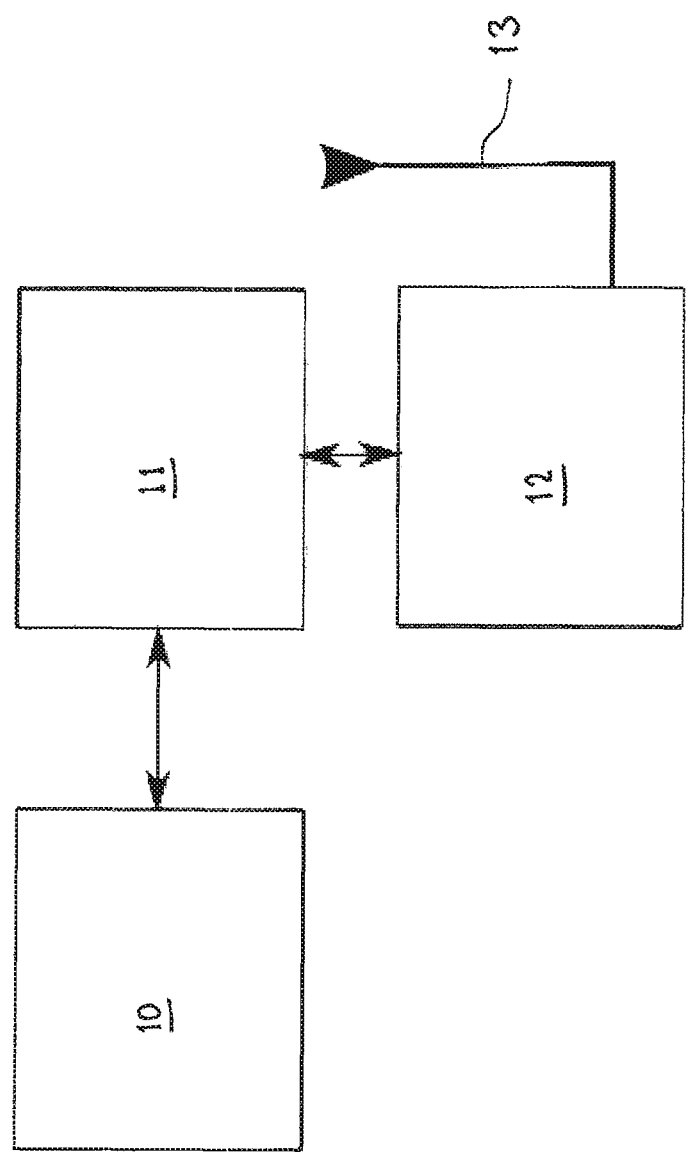
FIG. 2 shows a block diagram of a magnetometric detector according to the invention.

The components of the magnetometric detector 5 are shown schematically in greater detail in the block diagram of FIG. 2. The magnetometric detector 5 comprises an array 10 of two or more (e.g. four) magnetometers 14, 15 (not shown in FIG. 2) that is sampled by a microprocessor 11. The microprocessor 11 normalizes the measurement results obtained from the magnetometer array 10 and forwards it to a transceiver 12 with an antenna 13 which, in turn transmits the information to the base unit 6. In a modified version of this embodiment, the magnetometric detector 5 is provided with a multiplexer rather than with a microprocessor 11 and the normalization is performed by a processor 18 in the base unit 6.

Each magnetometer 14, 15 in the array 10 of magnetometers 14, 15 measures the components $a_k^u$, $a_k^v$, $a_k^w$ (k indicating the respective magnetometer) of the magnetic field at the position of the respective magnetometer 14, 15 in three linearly independent directions. The microprocessor 11 transforms these raw values $$a_k = (a_k^u, a_k^v, a_k^w)$$

into corresponding normalized values $$b_k = (b_k^x, b_k^y, b_k^z)$$

in predetermined orthogonal directions of equal gain by multiplying the three values $a_k$ obtained from the magnetometer with a normalisation matrix $M_k$ and adding a normalisation offset vector $\beta_k$:

$$b_k = a_k * M_k + \beta_k$$

This same transformation is performed for all magnetometers with their respective normalisation matrix and adding a normalisation offset vector such that the result $b_k$ for each magnetometer provides the components of the magnetic field in the same orthogonal spatial directions with identical gain. Thus, in a homogenous magnetic field, all magnetometers always provide identical values after normalisation regardless of the strength or orientation of the homogenous magnetic field. The normalisation matrices and the normalisation offset vectors are permanently stored in a memory associated with the microcontroller.

Figure 3:
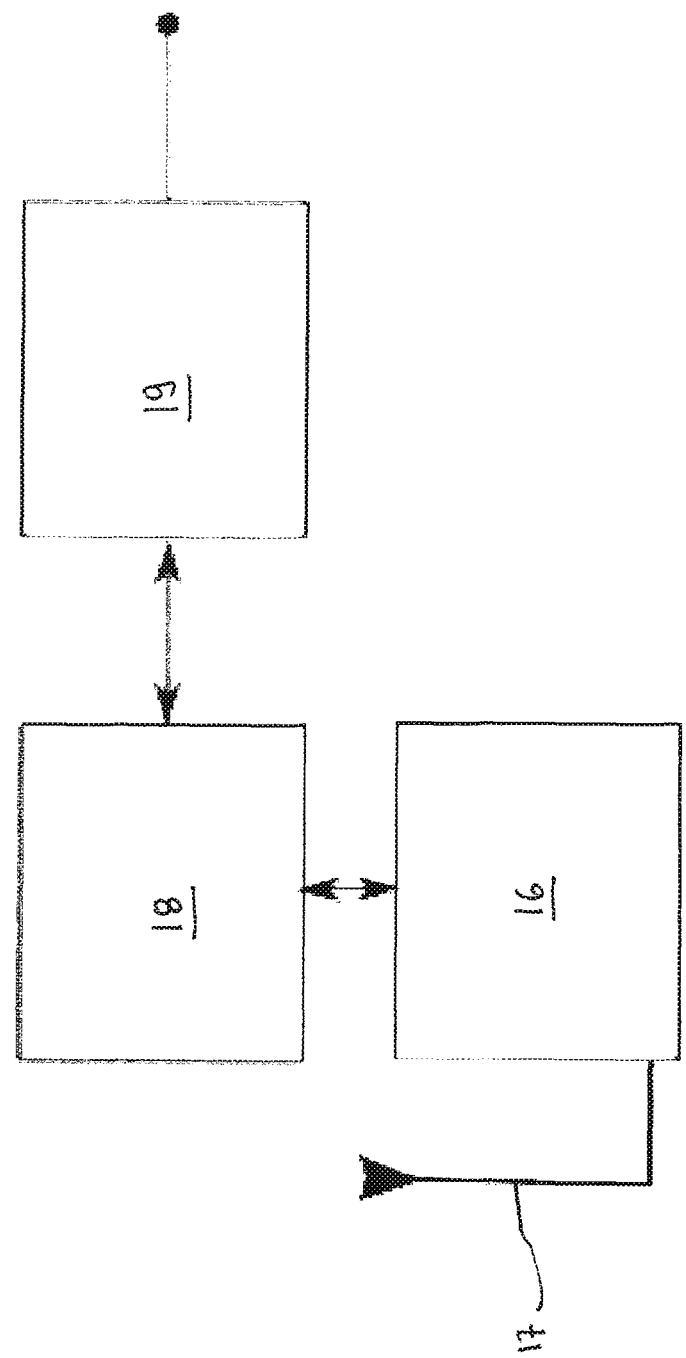
FIG. 3 shows a block diagram of a base unit according to the invention.

The base station 6 shown schematically in greater detail in FIG. 3 receives the normalised positional information from the magnetometric detector 5 through its receiver 16 with antenna 17 and forwards the information to a processor 18. There, the normalized results of the measurements are combined to derive the position (or position and orientation) of the cannula 8. For this purpose, the values $b_k$ are fit to a model of the combined magnetic field originating from the magnetic cannula 8 and the terrestrial magnetic field. The unknown parameters p in this model are the cannula's location 1 relatively to the ultrasound probe, it's length and orientation d and it's magnetic coercivity m as well as the terrestrial magnetic field E:

$$p = \{l, d, m, E\}.$$

The unknown parameters are obtained by means of the model of the magnetic field of the magnetic cannula and the terrestrial magnetic field, wherein $$c_k(p) = (c_k^x(p), c_k^y(p), c_k^z(p))$$

are the normalized components of the magnetic field according to the model at the position of magnetometer k at a given set of parameters p. By means of appropriate algorithms known to the skilled person the parameters p are obtained at which the deviation of the components of the magnetic field according to the model from the components actually measured $$\Sigma_k (b_k - c_k(p))^2$$

is minimized. Suitable minimization techniques are for example gradient-descent algorithms as well as Levenberg-Marquardt approaches. Moreover, Kalman filter techniques or similar iterative means can be utilized to continuously perform such an optimization.

If the cannula is sufficiently rigid, i.e. it does bend only slightly, it can be approximated as a straight hollow cylinder. The magnetic field of such cylinder is equivalent to that of opposite magnetic charges (i.e. displaying opposite magnetic force) evenly distributed on the end surfaces of the cylinder, i.e. two circular rings at the opposite ends of the cannula, the rings having opposite magnetic charge. In view of the small diameter of the cannula, the charges can further be approximated by two magnetic point charges at the opposite ends of the cannula. Thus, according to the model, the magnetic field of a cannula extending along the vector d is measured from a position $r_k$ is $$N(r_k, d, m) = m * (r_k/|r_k|^3 - (r_k + d)/|r_k + d|^3).$$

Here $|r_k|$ and $(|r_k + d|)$ indicate the absolute values of the vectors $r_k$ and $r_k + d$, respectively. The positions $r_k$ can be converted to the location 1 of the cannula 8 relatively to the ultrasound probe 2 with the help of the known positions of the magnetometers 14, 15 in the magnetometric detector 5 and the position of the magnetometric detector 5 relatively to the ultrasound probe 2. Consequently, further considering the terrestrial magnetic field E, the components of the magnetic field according to the model amount to $$c_k(p) N(r_k, d, m) + E = m * (r_k / < r_k|^3 - (r_k + d)/|r_k + d|^3) + E$$

Note that in contrast to many known approaches the above model does not assume the field of the needle to be a dipole field. This would be an oversimplification as the magnetometric detectors in general are too close to the needle as compared to the length of the needle to make a dipole field a valid approximation.

Figure 4:
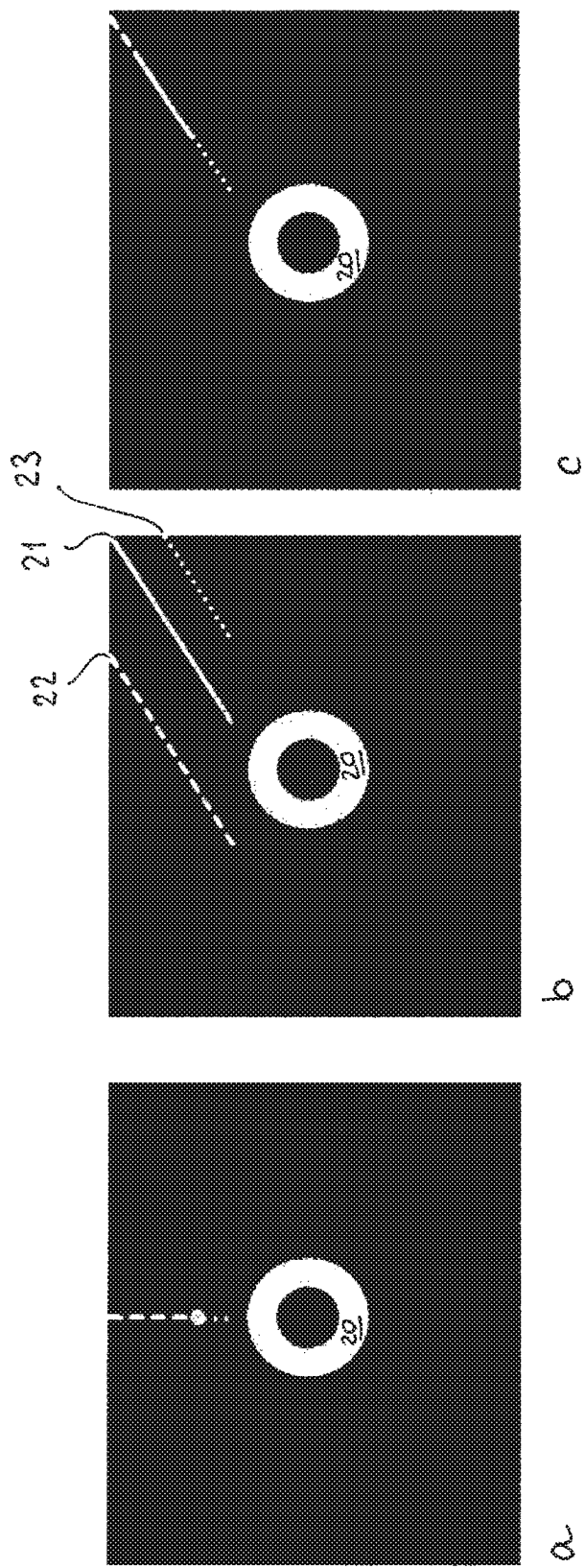
FIG. 4 shows schematically three examples of images of the patient's tissue with the position and orientation of cannula superimposed according to a first embodiment of the invention.

The values obtained by fitting the model to the actual values detected by the magnetometers 14, 15 as described above are then forwarded via data interface 19, e.g. a USB™ connector, to the processing unit 4. There, they are superimposed on the image of the tissue as obtained from the handheld ultrasound probe 2. The method of how the cannula 8 is visualized on the display screen is discussed with reference to FIG. 4. FIG. 4b shows the cross section of a blood vessel 20 as imaged by the hand held ultrasonic probe 2 in 2D mode. Accordingly, the blood vessel 20 cuts through the imaging plane of the ultrasound probe 2. Moreover, schematically, it is shown how the cannula 8 is visualized depending on its position relatively to the imaging plane. The cannula is always visualized as a line, the end of which corresponds to the cannula's tip. If the cannula 8 is within the probe's 2 imaging plane, it is, of a first colour (indicated as a full line 21 in the figures). If, on the other hand, the cannula 8 is outside the imaging plane, it is nevertheless shown, albeit in a different colour, the colour depending on whether the cannula 8 is in front of (colour indicated as a dashed line 22 in the figures) or behind the imaging plane (colour indicated as a dotted line 23 in the figures). FIG. 4a shows the situation when the cannula 8 cuts through the imaging plane. In this case, the section of the cannula 8 behind the imaging plane is shown in a different colour than the part of the cannula 8 that cuts through the plane which again has a different colour to the part of the cannula 8 that is in front of the imaging plane. The situation in FIG. 4c differs from that in FIG. 4a only in that the cannula 8 cuts through the plane in a different angle. The sections of the cannula 8 outside the imaging plane are shown on the display as their projections vertically onto the imaging plane.

In another embodiment, the whole expected needle track is shown on the image display, as described above. The actual position of the needle is indicated either by a different colour or line style (bold/hatched/etc) of the needle track. Furthermore, the point of cutting through the imaging plane might be indicated by a special graph for example, either the circle shown in FIG. 4a or a rectangle. The form or appearance of the graph might change to indicate the probability of the needle piercing the plane at that point, i.e. instead a circle a general ellipse might be used to indicate the target area.

Figure 5:
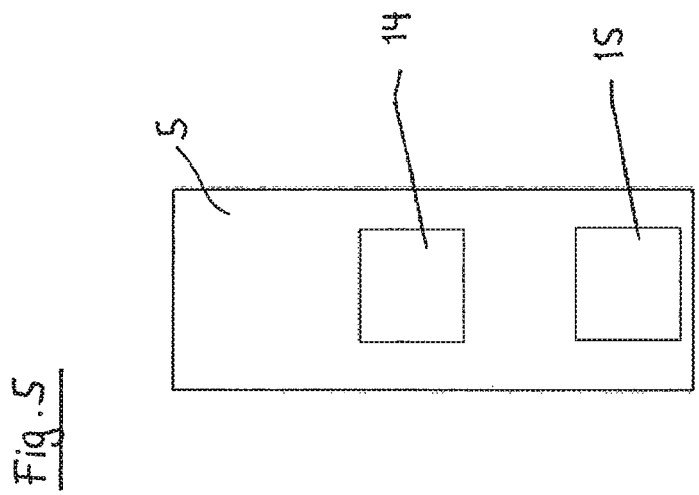
FIG. 5 shows schematically a magnetometric detector according to a second embodiment of the invention.
Figure 6:
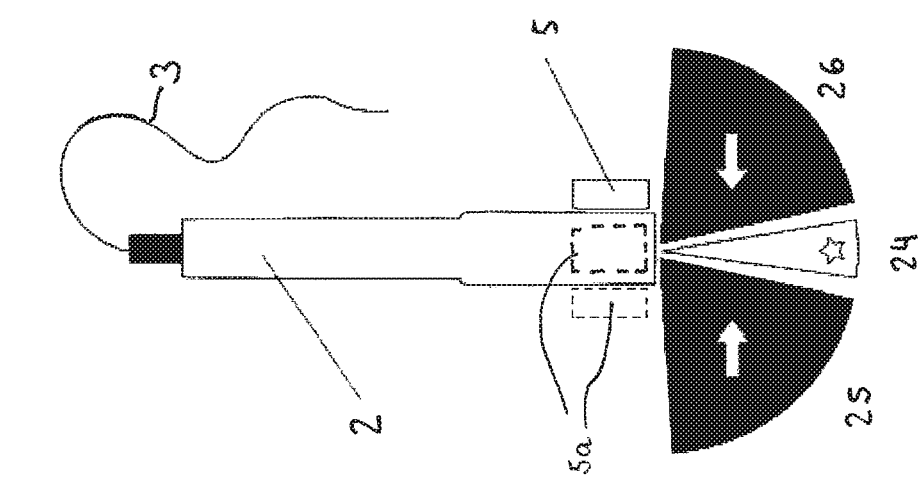
FIG. 6 shows a system of an ultrasound imaging probe and the magnetometric detector according FIG. 5.

An alternative embodiment of the magnetometric detector is shown in FIGS. 5 and 6. This magnetometric detector in a first variant of the embodiment only comprises a set 5 two magnetometers 14, 15. In an alternative variant of the embodiment one or more further sets are provided in further locations on the ultrasound probe 2. It is possible to derive whether the cannula 8 is located within the imaging plane 24, in front of 25 the imaging plane or behind 26 the imaging plane 24. For this purpose, the magnetometers are arranged along a line parallel to the probe's longitudinal axis. The normalized measurement results of the first magnetometer 14 are subtracted from those of the second magnetometer 15, thereby effectively cancelling out the terrestrial magnetic field. The difference is essentially pointing into the direction of the needle tip, because the other field component, caused by the end of the needle, is rapidly decaying in distance from the sensor arrangement. Thus, the sensor essentially "sees" only the needle tip. A relative distance can be inferred through the magnitude of the measured difference field.

In another embodiment of the invention, the magnetometers 14,15 are arranged perpendicular to the probe's longitudinal axis. Thus, the difference obtained essentially is the gradient of the magnetic field generated by the magnetic cannula 8. By analyzing the magnitude of the gradient, a relative distance of the cannula from the sensor can be elucidated. By analyzing the direction of the gradient it can be elucidated if the cannula 8 is in front of 25 or behind 26 or directly on the imaging plane 24.

Figure 7:
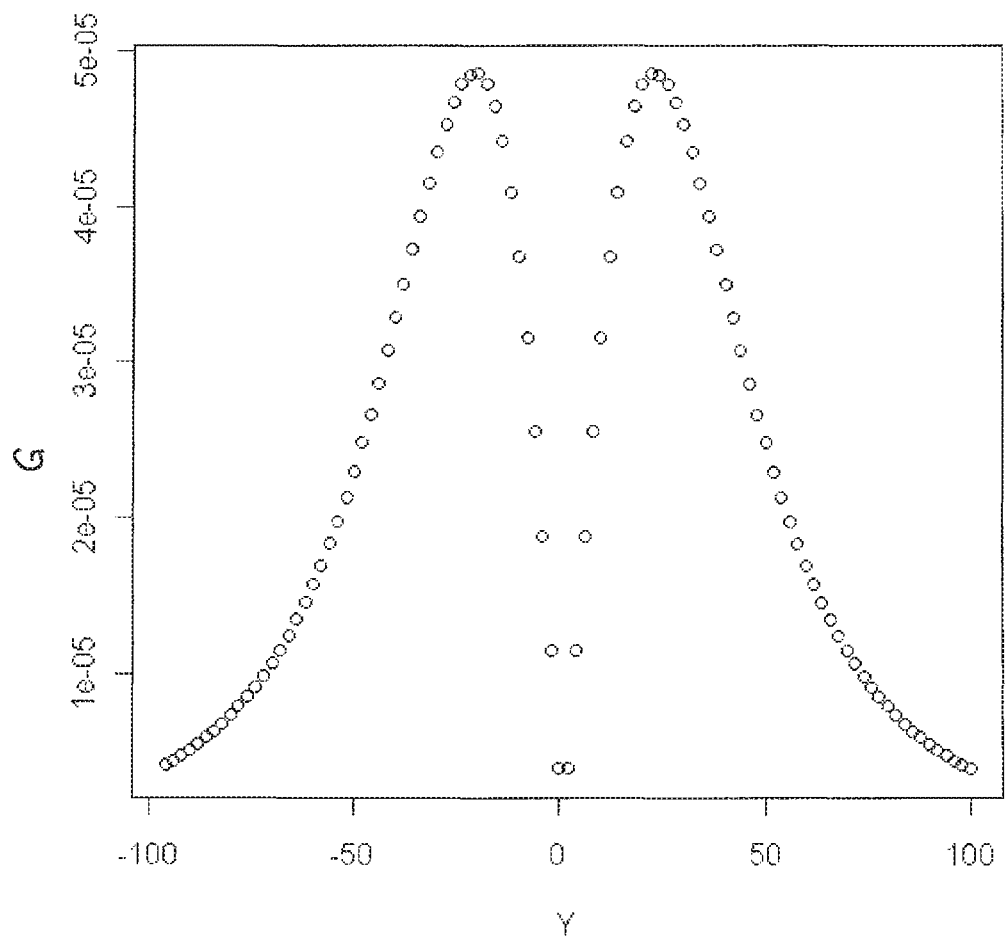
FIG. 7 shows the absolute gradient field strength in the embodiment of FIGS. 5 and 6 as a function of the needle's distance from the imaging plane of the ultrasound imaging plane.

FIG. 7 shows the absolute gradient field strength G (in arbitrary units) of a cannula 8 that extends in parallel to the imaging plane 24 but at a distance Y (in arbitrary units) from this plane 24. As can be seen, the gradient field strength G has a minimum if the distance Y equals 0, that is if the cannula 8 is in the imaging plane 24. If, on the other hand, the gradient field strength G is above a certain threshold, the cannula 8 can be assumed to be outside the imaging plane 24. In this case, the direction of the gradient field indicates whether the cannula 8 is in front of 25 or behind 26 the imaging plane 24 (this is not shown in FIG. 7 as the figure only shows the absolute value of the field). Thus, this simple setup can be used to for example superimpose on the ultrasound image displayed on the screen of the processing device the cues "*" (in plane), "=>" (in front of the imaging plane) or "<=" (before the imaging plane) even though the exact location and position of the needle of course cannot be indicated.

Figure 8:
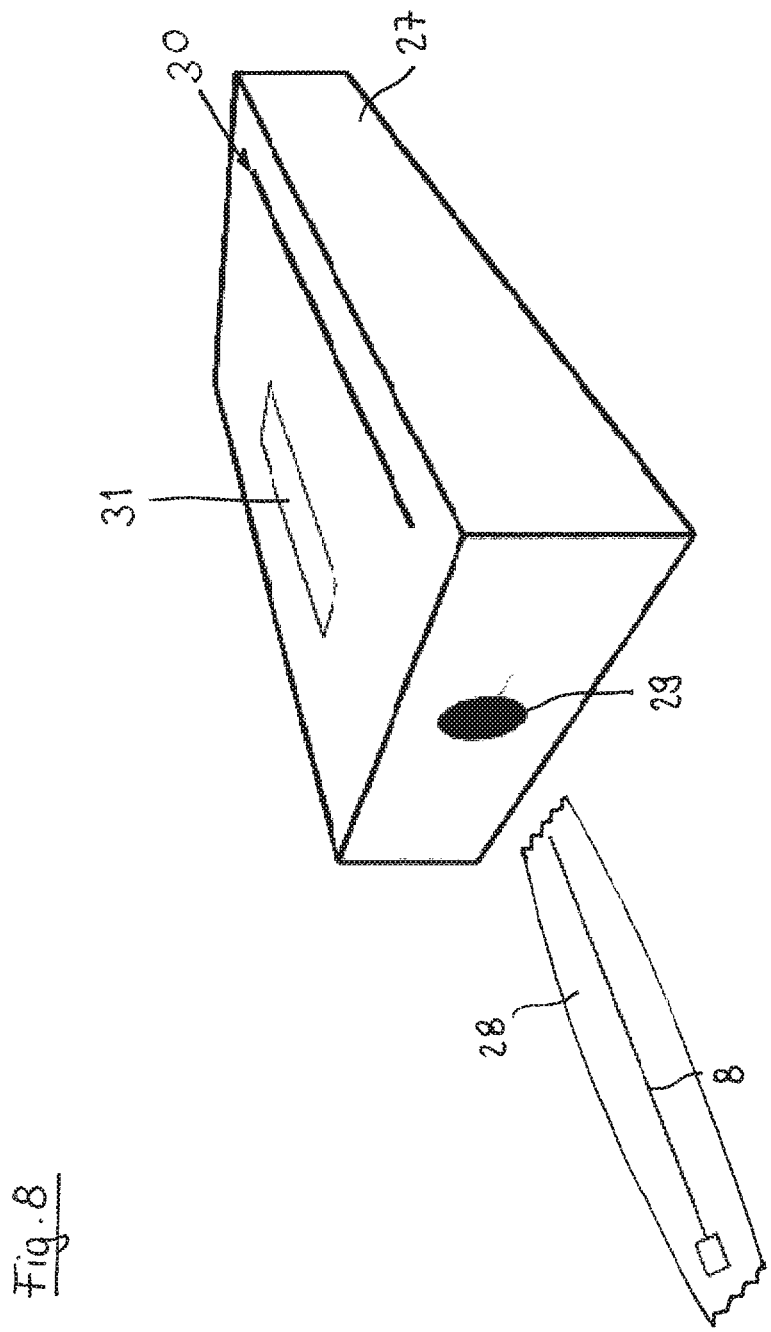
FIG. 8 shows a magnetization apparatus for magnetizing a cannula according to the invention.

Finally, FIG. 8 shows an apparatus 27 for magnetizing cannulae 8 according to the invention. Inside the box-shaped apparatus is a reservoir (not shown) which can hold a number of cannulae 8, each cannula 8 enclosed in a separate sterile film packaging 28. The apparatus 27 moreover comprises a round opening 29 through which individual cannulae 8 with their film packaging 28 can removed from the reservoir. On the inside, the opening is surrounded by a ring-shaped solenoid electromagnet (not shown). The electromagnet is powered by a power supply (not shown) attached to the apparatus. A switch on the power supply can electrify the electromagnet and thus turn on an electromagnetic field. Then, if a cannula 8 is removed from the box through the opening, it is at the same time magnetized.

Appropriate modulation of the electromagnet's current will allow coded magnetization as the needle is with-drawn from the reservoir.

Alternatively, the opening is one side of a hollow cylinder composed of separate magnetizing coils which allow imprinting a magnetic code onto the medical device in one step.

Subsequently, in order to measure the cannula's 8 magnetic moment and length, it is, still enclosed in the transparent sterile film packaging 28, placed on a line-shaped marking 30 on the apparatus 27. The ultrasound probe 2 within the attached magnetometric detector 5 is placed on another, box-shaped, marking 31 on the apparatus 27. As, from this, the relative position and orientation of the magnetometric device 5 and the cannula 8 is known, the magnetic moment and the length of the cannula can easily be derived from the measurements of the magnetometers 14, 15 after normalization. These values can then be used during the medical procedure to facilitate deriving the position and orientation of the cannula 8 from the measurements of the magnetometers by means of the above-described model.

The features described in the above description, claims and figures can be relevant to the invention in any combination.

The invention claimed is:
1. A medical device with a cannula which is insertable into the tissue of a patient, the cannula comprising a functional component of the medical device, the cannula formed at least in part of a material that can be magnetized,
  wherein the cannula has recorded along its length a coded magnetization pattern formed by a magnetic moment which varies in at least one of magnitude and direction as a function of location on the cannula, the coded magnetization pattern constituting a one-dimensional or more-dimensional magnetically-coded identification pattern on the cannula.

2. The medical device according to claim 1, wherein the functioning of the medical device does not depend on the cannula being magnetic.

3. The medical device according to claim 1, wherein the cannula is at least partly a permanent magnet.

4. The medical device according to claim 1, wherein the cannula or part of the cannula comprises a magnetic coating.

5. The medical device according to claim 1, wherein the cannula is made of steel.

6. The medical device according to claim 1, wherein the cannula is made of spring steel.

* * * * *